United States Patent [19]

Allington

[11] Patent Number: 4,536,091
[45] Date of Patent: Aug. 20, 1985

[54] ABSORBANCE MONITOR

[75] Inventor: Robert W. Allington, Lincoln, Nebr.

[73] Assignee: ISCO, Inc., Lincoln, Nebr.

[21] Appl. No.: 44,763

[22] Filed: Jun. 1, 1979

[51] Int. Cl.³ ............................................. G01N 21/01
[52] U.S. Cl. .................................... 356/435; 250/205; 250/573
[58] Field of Search ......................... 356/432, 435–437, 356/439, 440, 442, 71, 222, 223, 408, 411, 73; 250/573, 575, 578, 205

[56] References Cited

U.S. PATENT DOCUMENTS

| 3,422,271 | 1/1969 | Fuhrmann | 356/411 X |
| 3,777,173 | 12/1973 | Landrith | 250/575 |
| 4,025,199 | 5/1977 | Akami | 356/420 |
| 4,076,420 | 2/1978 | De Maeyer et al. | 356/73 |
| 4,080,075 | 3/1978 | Berg | 356/435 X |

OTHER PUBLICATIONS

Smith, W. J., "Modern Optical Engineering", McGraw-Hill, N.Y., 1966, pp. 20 and 21.

Primary Examiner—Bruce Y. Arnold
Attorney, Agent, or Firm—Vincent L. Carney

[57] ABSTRACT

To reduce noise in an absorbance monitor in which the light source is a feedback controlled deuterium lamp, a mirror focuses light from a part of the central bright spot in the deuterium lamp through a small aperture in an aperture plate which blocks all other light passing through the optical detecting and electrical sensor station. The light passing through the aperture is split into two unpolarized beams within the optical detecting and electrical sensor station, one of which is transmitted through an aperture optically at least as large as the image of the aperture near the lamp and into a flow cell to sense the absorbance or transmittance of an effluent. After the sensing beam has passed through the effluent, it is electrically compared with the other beam which has been passed through an aperture to cancel out the common-mode noise and in some applications the absorbance or transmittance which may be due to the solvent or other carrier of the sample.

19 Claims, 3 Drawing Figures

ABSORBANCE MONITOR

This invention relates to light absorbance monitors.

In one class of light absorbance monitor, light from a gas tube discharge lamp is split into two beams. One of the beams of light is passed through an effluent to sense the absorbance of the effluent and the other is used as a reference beam.

After the sensing beam of light has passed through the effluent, both beams are converted to electrical signals. The electrical signals are compared to remove the indications relating to the reference values and common-made noise, leaving a signal which is indicative of the absorbance or the transmittance of light. The signal is processed to obtain a visible indication of the effluent's light absorbance or light transmittance. This indication may be recorded or simply indicated on a meter.

In a prior art absorbance meter of this type, the light source is a low pressure mercury vapor lamp. Noise is reduced from the light in this lamp prior to splitting the beam by passing it through an aperture which may or may not include a fluorescent screen.

This type of absorbance monitor has a disadvantage in that some noise remains which relates to fluctuations in common-mode light intensity. Moreover, the frequency selection of light from such sources is limited.

Accordingly, it is an object of the invention to provide a novel radiation monitor.

It is a further object of the invention to provide a novel light monitor for radiation having a gas discharge lamp as its light source.

It is a still further object of the invention to provide a novel absorbance monitor having low noise characteristics.

It is a still further object of the invention to provide a light source which eliminates noise in the light emitted in a beam except for common-mode noise.

It is a still further object of the invention to provide a novel gas discharge light source with low noise except for common-mode noise.

It is a still further object of the invention to provide an inexpensive light source which removes noise from the beam of light except for common-mode noise.

In accordance with the above and further objects of the invention, a light absorbance monitor includes a gas discharge light source, an optical detecting and electrical sensor station and a common-mode noise cancellation circuit. In the gas discharge lamp light source, a condensing system focuses light from a small spot within the central bright spot of the gas discharge lamp onto a small aperture in an aperture plate which blocks all other light from the lamp. The intensity of the light is regulated by a feedback circuit from the common-mode noise cancellation circuit to reduce fluctuations.

The light which is passed through the small aperture in the light source is reflected by an aspheric focusing mirror onto a monochromator grating which selects the frequency of light to be applied to the sample being measured. The light from the monochromator is transmitted to a beam splitter, which splits the beam into two beams, one of which is to be used as a sensing beam for the transmittance or absorbance of the sample and the other of which is a reference beam. The beam splitter is of a type which provides as little plane polarization of the light as possible.

The sensing beam from the beam splitter is transmitted through a cell containing the sample after having the image of the aperture near the light source focused entirely through a small aperture which is part of the aperture stop of the samples. Similarly, the reference beam is passed through a similar aperture onto a photocell. A reference cell containing a solvent or the like without the sample may also be interposed in that beam under some circumstances.

In the common-mode noise cancellation circuit, two electrical signals, one resulting from the sensing beam of light after passing through the sample in the optical detecting and electrical sensing station and the other being a reference electrical signal from the reference beam of light, are ratio-compared to remove the common-mode noise, the resulting signal being used as an indication of the absorbance or transmittance of the sample. Within the common-mode noise cancellation circuit is a circuit to generate the logs of the measurement and reference signals. The log reference signal output from this circuit is fed back to the lamp intensity control to reduce common-mode noise which is otherwise incompletely cancelled due to lack of ideal balance of the sample and reference signals. Unexpectedly, the log circuit improves stability instead of reducing it as would normally be the case with a log circuit. This would be expected to happen because the gain of a log circuit is inversely proportional to the signal level and therefore shows extremely wide variations as the signal varies. Apparently it improves stability instead, because it always causes a given percent or ratio change in lamp level to produce the same absolute change output feedback voltage.

From the above description, it can be understood that the light absorbance monitor of this invention has several advantages such as: (1) it is economical and simple in construction; and (2) it removes substantially all noise except common-mode noise inexpensively in the light source and then removes the common-mode noise electrically in an advantageous manner.

The above noted and other features of the invention will be better understood from the following detailed description when considered with reference to the accompanying drawings in which.

Figure 1:
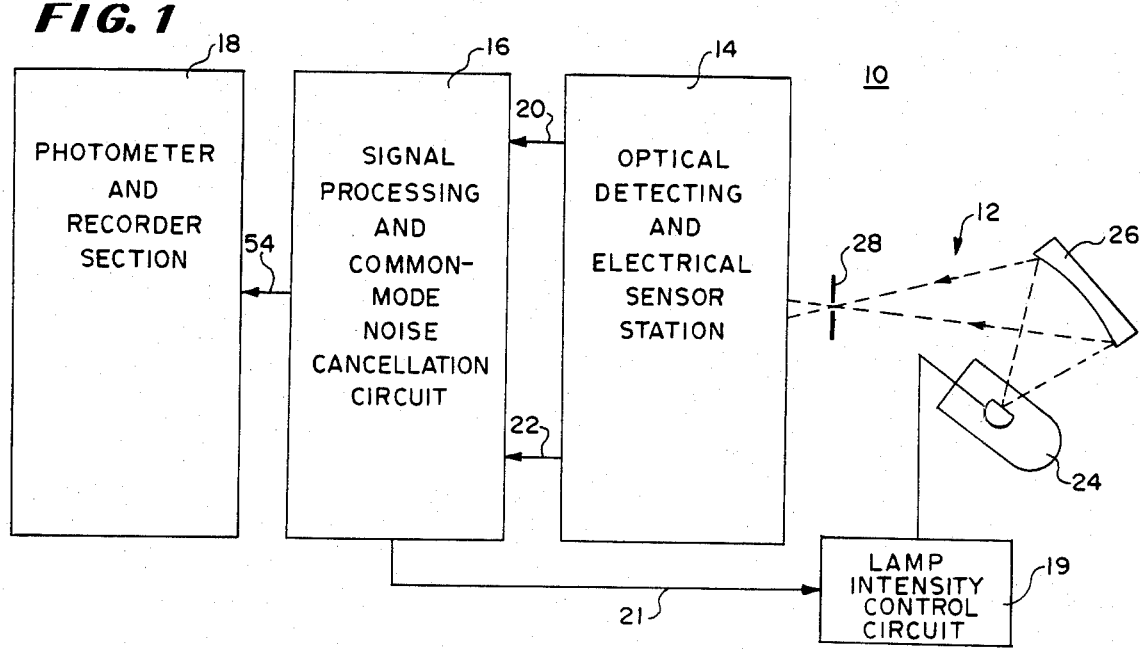
FIG. 1 is a block diagram of an absorbance monitor having a light source in accordance with an embodiment of the invention.

In FIG. 1, there is shown a block diagram of a light absorbance monitor 10 having a light source 12, an optical detecting and electrical sensor station 14, a signal-processing and common-mode noise cancellation circuit 16, a photometer and recorder section 18, and a lamp intensity control circuit 19.

The light source 12 generates a beam of light which has noise present in it due to fluctuations originating in the gas discharge lamp and transmits that beam of light to the optical detecting and electrical sensor station 14. The optical detecting and electrical sensor station 14 splits the beam of light and senses an effluent concentration and the lamp noise with one beam, designated the measuring beam, while using the other beam as a reference beam which senses lamp noise alone. The light is detected by a sensor and electrical signals are transmitted through conductors 20 and 22 to the signal-processing and common-mode noise cancellation circuit 16. These electrical signals carry information about the effluent or other material sensed in the optical detecting and electrical sensor station 14 by the beam of light from the light source 12.

The signal-processing and common-mode noise cancellation circuit 16 removes the common-mode noise and performs other routine processing on the signal before transmitting it to the photometer and recorder section 18 which records or indicates the information and therefore the material through which it has been passed for monitoring of absorbance. The lamp intensity control circuit 19 is electrically connected to the cathode of deuterium lamp 24 and controls the power applied to the lamp to thus regulate the lamp and reduce fluctuations in intensity. It is controlled by feedback from the signal-processing and common-mode noise cancellation circuit 16 through a conductor 21.

To provide a beam of light to the optical detecting and electrical sensor station 14, the light source 12 includes a deuterium lamp 24, a mirror 26 and an aperture plate 28. The mirror 26 is an aspheric condensing mirror positioned to focus the image of a small portion of the source of the deuterium lamp 24 onto a small aperture in the aperture plate 28, which is positioned between the lamp 24 and the optical detecting and electrical sensor station 14. Advantageously, the small portion of the source is a portion of the central bright spot and this portion of the central bright spot is focused on the aperture, which is approximately 1 millimeter in diameter.

Light from portions of the lamp 24 that is not focused through the aperture in aperture plate 28 may have intensities of light transmitted in different directions which vary with respect to each other. Such light is either not received by the mirror or reflected in directions which are not focused directly on the aperture in the plate 28 so that a high intensity light from a single small spot in the central bright spot of deuterium lamp 24 is focused on the aperture in the aperture plate 28, all other light being blocked from the optical detecting and electrical sensor station 14 by the plate.

While an aspheric condensing mirror 26 is shown, it is obvious that a lens or groups of lenses and mirrors may be used. The feature that is significant is that the light from a single spot in the lamp 24 is focused directly on the aperture in the plate 28 to provide a strong beam of light from one spot which dominates the light passing through the aperture plate 28 to the optical detecting and electrical sensor station 14. This light may include common-mode noise due to variation of the light at the one point which is focused on the aperture in the aperture plate 28 but light fluctuations in the intensity of light in one direction with respect to the intensity in another direction does not affect the beam being passed to the optical detecting and electrical sensor station 14 since only light from the one spot passes the aperture plate 28 with any significant intensity.

Figure 2:
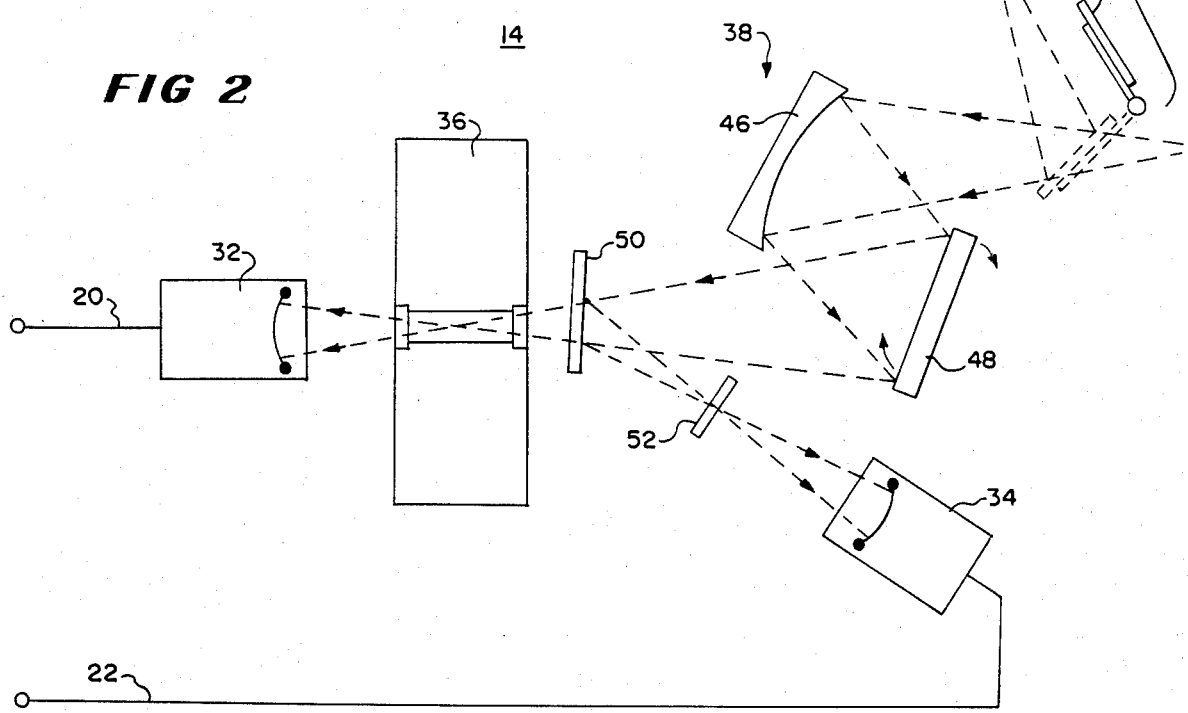
FIG. 2 is a schematic diagram of a portion of the embodiment of FIG. 1.

In FIG. 2, there is shown a schematic diagram of the optical detecting and electrical sensor station 14 having measuring and reference photosensors 32 and 34 respectively, a flow cell 36 and an optical system 38.

The optical system 38 receives light from the light source 12 (FIG. 1) and processes the beam to select a specific frequency, after which it splits the beam into two beams, one of which is applied through the flow cell 36 and onto the measuring photocell 32 and the other of which is applied to the reference photocell 34. A second reference flow cell or reference sample may be positioned in the beam that is applied to the photocell 34 although one is not shown in FIG. 2. The optical detecting and electrical sensor station 14 also includes an incandescent lamp section 40 having a tungsten-krypton lamp 42 and a pivotable mirror 44.

The optical system 38 includes an aspheric focusing mirror 46, a diffraction grating assembly 48, a beam splitter 50, and an aperture plate 52. The aspheric focusing mirror 46 is positioned to receive the light from the light source 12 (FIG. 1) and focus it upon the diffraction grating assembly 48.

The diffraction grating assembly 48 serves as a monochromator and includes a reflective diffraction grating which may be pivoted to change the frequency of light it selects. The beam splitter 50 is positioned between the reflected light from the diffraction grating assembly 48 and the windows of the flow cell 36 to permit light to pass from the diffraction grating assembly 48 through the flow cell and to focus another beam downwardly.

The aperture plate 52 is between the second beam formed by the beam splitter 50 and the reference photocell 34 so that one beam of light passes through the flow cell and on to the measuring photocell 32 and the other beam of light impinges upon the reference flow cell 34 after passing through an aperture plate which simulates the aperture stop of the flow cell 36.

In the preferred embodiment the beam splitter 50 is a quartz plate positioned to split the beam without polarizing the light. For this purpose it is positioned at an angle sufficiently close to being normal to the incident light to make the amount of plane polarization of the light negligible but yet at a sufficient angle to provide beam splitting with a reflection of light to the reference photocell 34. It is desirable to prevent plane polarization because it has been found that such polarization increases noise since apparently light from the light source apparently varies in intensity along different axes of polarization.

A ten degree deivation from normal to provide reflected light twenty degrees from the incident light has been found to be suitable for the quartz plate and to be sufficiently far from the Brewster angle so that the component of plane-polarized light is negligible. Of course, any other technique for providing two beams of light from the one beam of light without significant polarization is suitable.

The flow cell 36 includes an aperture stop which is the same size as the aperture in the aperture plate 52. The size of the aperture is such that the image of light passing through the aperture plate 28 (FIG. 1) may be focused within the apertures in the flow cell 36 and the aperture plate 52. In the preferred embodiment, the optical system between aperture plates provides magnification of one and one-half times. Thus, the aperture in the plate 52 and the aperture provided by the aperture stops of the flow cell 36 is 1.5 millimeters in diameter so that the image of the aperture in the plate 28 (FIG. 1) which is one millimeter in diameter may fall within it.

The pivotable flat mirror 44 in the calibration assembly 40 may be pivoted to an upward position so as to permit light from the light source 12 (FIG. 1) to pass or may be pivoted downwardly so as to block that light and instead reflect light from the tungsten-krypton lamp 42 to the focusing mirror 46. This alternate source of light is not part of the invention.

The conductor 20 is electrically connected to the photosensor 32 to provide an electrical signal which is representative of the light absorbance by the material in the flow cell 36 and the conductor 22 is electrically connected to the photocell 20 to provide a reference signal which is equivalent to the light. These signals are connected to the signal-processing and common-mode noise cancellation circuit 16 (FIG. 1).

Figure 3:
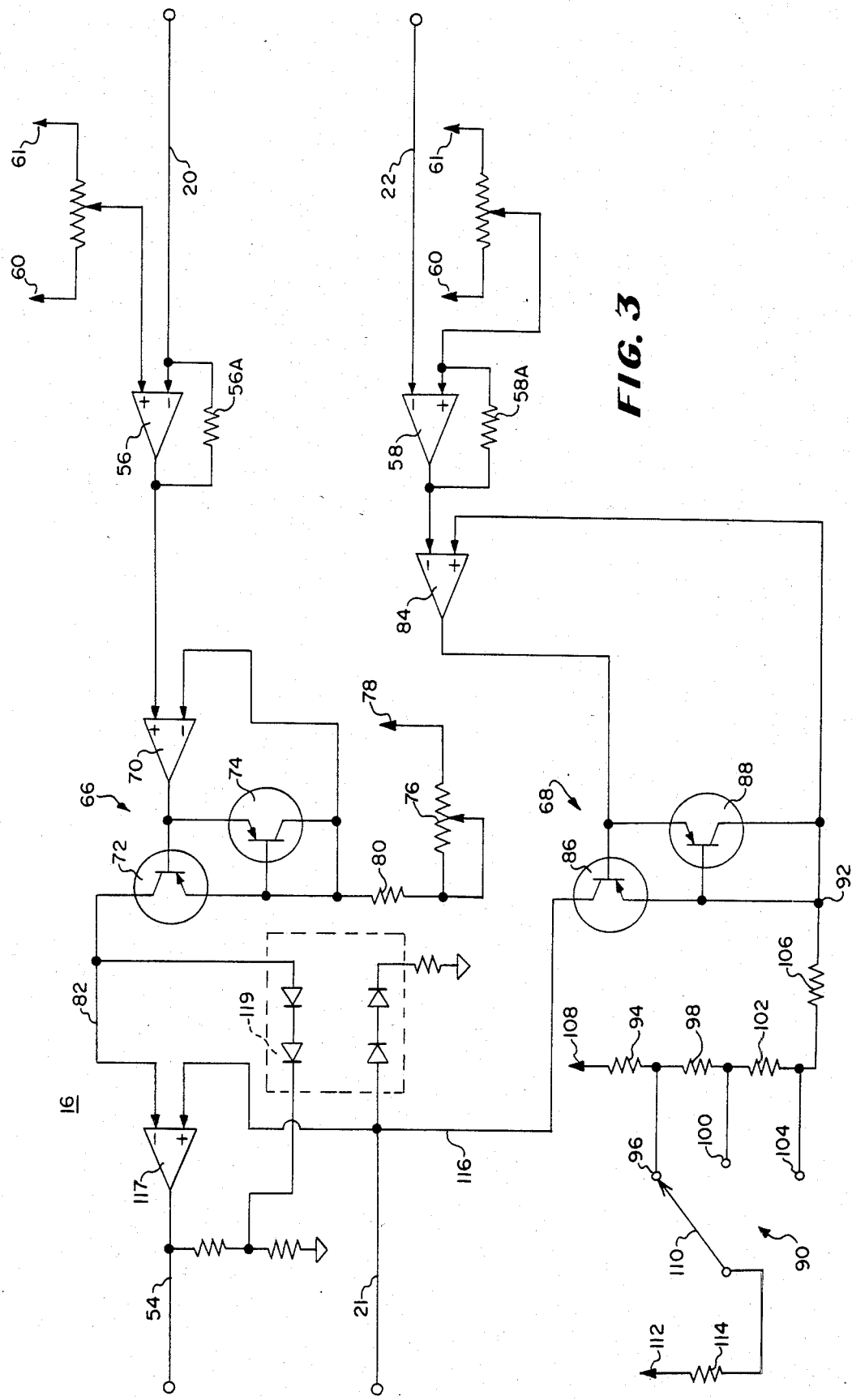
FIG. 3 is a schematic circuit diagram of still another portion of the embodiment of FIG. 1.

In FIG. 3, there is shown a schematic circuit diagram of the signal-processing and common-mode noise cancellation circuit 16 for receiving the measuring electrical signals on conductor 20 and the reference signal on 22, cancelling noise and applying an output signal to the photometer and recorder section 18 (FIG. 1) through a conductor 54. The photometer and recorder section plays no part in this invention except to receive the signal and otherwise may operate in the manner of any photometer and recorder section of an absorbance monitor.

The photocurrents from the measuring and reference photodetectors are led respectively to the inverting inputs of differential amplifiers 56 and 58. Feedback resistors 56A and 56B determine the gain of the amplifiers.

To correct the signals on conductors 20 and 22 for dark current from the photocells, the signal-processing and common-mode noise cancellation circuit 16 includes means for subtractive cancellation of the dark current.

To provide a signal for subtraction from the signals on conductors 20 and 22, the differential amplifier 56 has its positive or noninverting input electrically connected to a source of adjustable potential through an adjustable potentiometer 62 leading to a pair of fixed potentials generally indicated as 60 and 61. The amplifier 58 has its positive or noninverting input terminal electrically connected to the source of adjustable potential through an adjustable potentiometer 64. The negative or inverting input terminal of differential amplifier 56 is electrically connected to conductor 20 and the negative or inverting input of differential amplifier 58 is electrically connected to the conductor 22.

To adjust the amplitude of the signals to be subtracted to compensate for dark current, the potentiometers 62 and 64 are adjusted with no illumination on the photoconductors to cancel the dark current from the photosensors 32 and 34 (FIG. 2). With this adjustment, the dark current is removed during the reception of light by the photocells.

To adjust the baseline and convert the voltage signal to a current signal, the signal-processing and common-mode noise cancellation circuit 16 includes a fine baseline adjust circuit 66 and a coarse baseline adjust circuit 68, each of which have incorporated in them a different voltage-to-current converter.

The fine baseline adjust circuit 66 includes a differential amplifier 70, a first PNP transistor 72, a second PNP transistor 74 and an adjustment potentiometer 76. The output of differential amplifier 56 is electrically connected to the positive input of differential amplifier 70.

To provide voltage-to-current conversion of the signal: (1) the base of PNP transistor 72 and the emitter of PNP transistor 74 are electrically connected to the output of differential amplifier 70; and (2) the collector transistor 74, the base of transistor 74, and the emitter of transistor 72 are electrically connected to the inverting or negative input terminal of differential amplifier 70.

To provide fine adjustment of the baseline, a source of positive potential 78 is connected through the adjustable potentiometer 76 and a fixed resistor 80 and the negative input terminal of the amplifier 70 in series in the order named. The incoming signal to differential amplifier 70 is reduced by the signal to the negative input terminal of differential amplifier 70 which is adjusted by the potentiometer 76 to adjust the baseline. Adjustment of potentiometer 76 varies the emitter (and collector) current of transistor 72 in response to a given input voltage at the positive input terminal of amplifier 70, thus adjusting the baseline.

The coarse baseline correction circuit 68 includes the differential amplifier 84, a first PNP transistor 86, a second PNP transistor 88, and a coarse baseline correction stepping switch circuit 90. The positive or noninverting terminal of differential amplifier 84 is electrically connected to the output of differential amplifier 58.

To provide voltage-to-current conversion of the signal; (1) the output of differential amplifier 84 is electrically connected to the base of transistor 86 and to the emitter of transistor 88; and (2) the emitter of transistor 86, the base of transistor 88 and the collector of transistor 88 are each electrically connected to a terminal 92 of the coarse baseline adjustment switch 90.

To provide coarse adjustment of the baseline, the stator for the adjustment switch 90 includes a first resistor 94, a switch contact 96, a second resistor 98, a second switch contact 100, a third resistor 102, a fourth switch contact 104 and a fifth resistor 106 electrically connected in series in the order named between a source of negative potential 108 and the terminal 92. While four resistors and three switch contacts are shown and described, in the actual embodiment there are more fixed switch contacts and more resistors in the stepping switch to provide greater adjustment flexibility.

A switch arm or armature 110 of the adjustment switch 90 is electrically connected to a source of positive potential 112 through a resistor 114 to provide a variable resistance in series with the positive potential 108 to the differential amplifier 84 for coarse baseline correction. The collector of transistor 86 provides the corrected reference current signal on a conductor 116.

To convert the signals to logarithmic so as to represent absorbance, a matched diode log conversion circuit 119 is electrically connected to conductors 116 and 82 and conductor 116 is connected to conductor 21 to control the intensity of the light source 24 (FIG. 1). This circuit may be of the type described in U.S. Pat. No. 3,676,686 issued to Robert W. Allington to HIGH SENSITIVITY LIGHT ABSORBANCE APPARATUS on July 11, 1972. It is advantageous to use matched diodes in that circuit.

To eliminate common-mode noise, the signal-processing and common-mode noise cancellation circuit 16 includes a differential amplifier 117 having its inverting or negative input terminal electrically connected to the conductor 82 and its positive or noninverting terminal electrically connected to the conductor 116. The output of the differential amplifier 117 is also electrically connected to the conductor 54.

Conductor 54 receives the electrical sensing signal after correction by subtraction or cancellation of the reference signal, baseline errors and the dark current of the photocells, thus providing a signal to the photometer and recorder section 18 (FIG. 1) indicative of the absorbance of light in the flow cell. In this process, the common-mode noise coming from the gas discharge lamp is cancelled within the differential amplifier 117 between the reference signal and the measured signal.

Before operating the light absorbance monitor 10 (FIG. 1) to detect the light absorbance of the components of a sample, certain adjustments are made. One such adjustment is the cancelling of dark current in the photosensors 32 and 34. To accomplish this, the lamps are extinguished and the potentiometers 62 and 64 (FIG. 3) adjusted while the outputs from the amplifiers 56 and 58, or from each pair of the log diodes shown in FIG. 4 of U.S. Pat. No. 3,676,686, are measured until the dark currents have been cancelled within the differential amplifiers 56 and 58.

In operation, with the flat mirror 44 in the position shown in FIG. 2, the deuterium lamp 24 in the lamp source 12 (FIG. 1) is the source of illumination for the optical system 38 (FIG. 2) and the photosensors 32 and 34. The light radiated from the lamp fluctuates in intensity in two modes which are: (1) the arc within the deuterium lamp fluctuates in intensity position; and (2) the light is emitted with different fluctuating intensity from different parts of the lamp and the emitted light intensity in one direction fluctuates with respect to the intensity of light in another direction.

To prevent fluctuations in the intensity of light in the reference beam with respect to the sensing beam due to directional fluctuations in the lamp, the aspheric condensing mirror 26 is positioned such that the image of a small area covering a portion of the central bright spot in the arc is focused on the aperture of the aperture plate 28. With this arrangement, only a small portion of the arc passes substantial light intensity through the aperture plate 28. This light intensity fluctuates with the fluctuation of the single point in the arc within the deuterium lamp but there is no light transmitted with dissimilar fluctuations in intensity in different directions transmitted through the aperture plate 28 to the optical detecting and electrical sensor station 14.

The light entering the optical detecting and electrical sensor station, as best shown in FIG. 2, is focused by the aspheric focusing mirror 46 onto the diffraction grating assembly 48. The diffraction grating in that assembly is adjusted to reflect a selected frequency of light to the beam splitter 50 and through the windows of the flow cell 36 onto the measuring photocell 32.

The beam splitter 50 splits the beam of light, without significant polarization of it, and focuses a portion of it through the aperture in the aperture plate 52 onto the reference photosensor 34. The aperture stop in the flow cell 36 in front of the photocell forms an aperture for the light equivalent in size to the aperture in the aperture plate before the reference photocell, each being just large enough to receive within them the entire image of the aperture in the aperture plate of the light source. The photosensor 32 generates an electrical signal from the light passing through the flow cell 36 and applies it to conductor 20 and the photosensor 34 generates an electrical signal and a response to the light impinging upon it and applies it to the conductor 22.

Before the material which is to be studied in the absorbance monitor flows through the flow cell but usually after a solvent which is to carry the material has been applied, the baseline is adjusted. This is accomplished by switching the switch arm 110 of the coarse baseline adjustment stepping switch 90 (FIG. 3) until the baseline is fairly close to the desired level. The fine adjustment potentiometer 76 is then also adjusted. These adjustments may be made periodically during measurements to reduce baseline offset and increase the usable amplitude of the signal.

When the equipment is ready for a measurement, the effluent to be measured is permitted or caused to flow through the flow cell 36. The signal on conductor 20 now is altered in accordance with the absorbance of light by the effluent and by the solvent carrying the effluent whereas the conductor 22 carries a signal which is affected only by the solvent. Both signals may have common-mode noise originating with the light source 12 (FIG. 1).

To remove the common-mode noise, the signals on conductors 20 and 22, after they have passed through the differential amplifiers 56 and 58 respectively which remove the dark current from the photosensors where applicable and through the circuits 66 and 68 which adjust for baseline, are applied to the differential amplifier 117. There the signals are subtracted from each other which removes the reference from the signal caused by the effluent and at the same time removes the common-mode noise. Prior to subtraction in the differential amplifier, the signals are converted to the log of the signals in amplitude, using log converters. Feedback from the log converters controls the intensity of the light source.

This final signal is applied to conductor 54. It may be processed in ways known in the art in the photometer and recorder section 18 to provide indications of absorbance or transmittance of the effluent in the flow cell 36. Such processing is not part of this invention nor is the indicating on the detector or the recording since these are all well known in the prior art.

From the above description, it can be understood that the absorbance monitor of this invention has the advantage of removing noise caused by fluctuations of light within a gas discharge lamp with relatively inexpensive equipment and simple equipment.

Although a specific embodiment of the invention has been described with some particularity, many modifications and variations in the embodiment are possible without deviating from the invention. Therefore, it is to be understood that, within the scope of the appended claims. the invention may be practiced other than as specifically described.

What is claimed is:

1. A method comprising the step of:
   focusing light with a mirror from a small spot on the light emitting portion of a gas discharge lamp including at least a small portion of its central bright spot through an aperture in an aperture plate;
   splitting the light passing through the aperture plate into two beams of light without creating a polarization difference in the two beams of light;
   focusing one of said beams of light within a small aperture and using it to sense the characteristic of a sample and focusing the said other beam of light through an aperture of the same size with both apertures being of such a size as to contain within each of them the image of the aperture in the aperture plate, wherein said other beam of light serves as a reference;
   converting the beams of light into electrical signals after said one beam of light has been brought into intimate contact with the sample and comparing the signals to cancel common-mode noise; and
   converting said signals to the log form of the amplitude of the signals and feeding back at least the log of one of the signals to the light source to stabilize the light source.

2. A method comprising the steps of:
   focusing light with a mirror from a small spot on the light emitting portion of a light source through an aperture in an aperture plate;

splitting the light passing through the aperture plate into two beams of light without creating a polarization difference between the two beams of light;

focusing one of said beams of light within a small aperture and using it to sense the characteristic of a sample and focusing the said other beam of light through an aperture of the same size with both apertures being of such a size as to contain within each of them the image of the aperture in the aperture plate, wherein said other beam of light serves as a reference;

converting the beams of light into electrical signals after said one beam of light has been brought into intimate contact with the sample and comparing the signals to cancel common-mode noise; and converting said signals to the log form of the amplitude of the signals and feeding back at least the log of one of the signals to the light source to stabilize the light source.

3. A method comprising the steps of:

focusing light from a small spot on the light emitting portion of a light source through an aperture in an aperture plate;

splitting the light passing through the aperture plate into two beams of light without creating a polarization difference in the two beams of light;

focusing one of said beams of light within a small aperture and using it to sense the characteristic of a sample and focusing the said other beam of light through an aperture of the same size with both apertures being of such a size as to contain within each of them the image of the aperture in the aperture plate, wherein said other beam of light serves as a reference;

converting said sensing signal and said reference signal into electrical signals after said one beam of light has been brought into intimate contact with the sample and comparing said electrical signals to cancel said common-mode noise; and converting said signals to the log form of the amplitude of the signals and feeding back at least the log of one of the signals to the light source to stabilize the light source.

4. A method comprising the steps of:

focusing light from a small spot on the light emitting portion of a light source through an aperture in an aperture plate;

splitting the light passing through the aperture plate into two beams of light without creating a polarization difference between the two beams of light;

focusing one of said beams of light within a small aperture and using it to sense the characteristic of a sample and focusing the said other beam of light through an aperture of the same size with both apertures being of such a size as to contain within each of them the image of the aperture in the aperture plate, wherein said other beam of light serves as a reference;

comparing the signals resulting from said beams of light after said one beam of light has been brought into intimate contact with the sample to cancel common-mode noise; and converting said signals to the log form of the amplitude of the signals and feeding back at least the log of one of the signals to the light source to stabilize the light source.

5. A method comprising the steps of:

focusing light from a small spot on the light emitting portion of a light source through an aperture in an aperture plate;

splitting the light passing through the aperture plate into two beams of light;

focusing one of said beams of light within a small aperture and using it to sense the characteristic of a sample and focusing the said other beam of light through an aperture of the same size with both apertures being of such a size as to contain within each of them the image of the aperture in the aperture plate, wherein said other beam of light serves as a reference;

comparing the signals resulting from said beams of light after said one beam of light has been brought into intimate contact with the sample to cancel common-mode noise; and converting said signals to the log form of the amplitude of the signals and feeding back at least the log of one of the signals to the light source to stabilize the light source.

6. A method comprising the steps of:

focusing light from a small spot on the light emitting portion of a light source through an aperture in an aperture plate;

splitting the light passing through the aperture plate into two beams of light;

using one of said beams of light to sense a characteristic of a sample and using the other beam of light as a reference;

comparing the signals resulting from said beams of light after said one beam of light has been brought into intimate contact with the sample to cancel common-mode noise; and converting said signals to the log form of the amplitude of the signals and feeding back at least the log of one of the signals to the light source to stabilize the light source.

7. A method comprising the steps of:

focusing light from a small spot on a light source into a beam of light;

splitting the beam of light into two beams of light;

bringing one of said two beams of light into intimate contact with a sample;

converting each of the two beams of light into electrical signals having amplitudes which are the log of the intensity of the beams of light;

feeding at least one of said signals back to the light source to control fluctuations in the light source; and comparing the two signals resulting from said two beams of light after said one beam of light has been brought into intimate contact with the sample to cancel common-mode noise.

8. A method according to claim 7 in which the step of splitting the light passing through the aperture plate into two beams of light comprises the step of splitting the beam of light into two beams of light without creating a polarization difference in the two beams of light.

9. A method comprising the steps of:

focusing light from a small spot on the light emitting portion of a light source into a beam;

splitting the light in said beam into two beams of light without creating substantial polarization of the light in either beam;

using one of said beams of light to sense a characteristic of a sample and using the other beam of light as a reference;

comparing the signals resulting from said two beams of light after said one beam of light has been brought into intimate contact with the sample to cancel common-mode noise; and converting said signals to the log form of the amplitude of the signal and feeding back at least the log of one of the signals to the light source to stabilize the light source.

10. Apparatus comprising:

a light source;

focusing means for focusing light from a first small spot on the light emitting portion of said light source onto a second small spot;

an aperture plate having a relatively small aperture in it;

said aperture plate being placed at said location where said aperture in it coincides with said second small spot;

said light source comprising a gas discharge lamp;

said gas discharge lamp having a central bright spot;

said focusing means including means for focusing light from at least a portion of the central bright spot of said gas discharge lamp onto said second small spot;

said focusing means including an aspheric concave mirror;

means for forming a beam of light from the light passing through said aperture and splitting said beam of light into first and second beams of light without substantial polarization of the light;

means for bringing said first of said beams of light into intimate contact with a sample;

means for converting said first of said beams of light into a first electrical signal after it has been brought into intimate contact with a sample;

means for converting the second of said beams of light into a second electrical signal;

means for comparing said first and second electrical signals to remove common-mode noise;

said means for splitting said beam of light into two beams of light including a quartz beam splitter positioned at an angle of approximately ten degrees from the incident light;

means for converting said first and second electrical signals into signals having an amplitude which is the log of the amplitude of said first and second signals; and feedback means for feeding the log of one of said first and second signals back to said light source for regulating the intensity thereof.

11. Apparatus comprising:

a light source;

focusing means for focusing light from a first small spot on the light emitting portion of said light source onto a second small spot;

an aperture plate having a relatively small aperture in it;

said aperture plate being placed at said location where said aperture in it coincides with said second small spot;

means for forming a beam of light from the light passing through said aperture and splitting said beam of light into first and second beam of light without substantial influence upon the polarization of the light;

means for bringing said first of said beams of light into intimate contact with a sample;

means for converting said first of said beams of light into a first electrical signal after it has been brought into intimate contact with a sample;

means for converting the second of said beams of light into a second electrical signal;

comparing said first and second electrical signals to remove common-mode noise;

said means for splitting said beam of light into two beams of light including a quartz beam splitter positioned at an angle of approximately ten degrees from the incident light;

said means for splitting a beam of light including aperture stops on a flow cell and an aperture plate;

said aperture stops and aperture plate having apertures in them for receiving respectively said first beam of light and said second beam of light;

said aperture stops and apertures being of such a size as to have the image of said aperture in said aperture plate fall within each of them;

means for converting said first and second electrical signals into signals having an amplitude which is the log of the amplitude of said first and second signals; and feedback means for feeding the log of one of said first and second signals back to said light source for regulating the intensity thereof.

12. Apparatus comprising:

a light source;

focusing means for focusing light from a first small spot on the light emitting portion of said light source onto a second small spot;

an aperture plate having a relatively small aperture in it;

said aperture plate being placed at said location where said aperture in it coincides with said second small spot;

means for forming first and second beams of light from the light passing through said aperture;

means for bringing said first of said beams of light into intimate contact with a sample;

means for converting said first of said beams of light into a first electrical signal after it has been brought into intimate contact with a sample;

means for converting the second of said beams of light into a second electrical signal;

means for comparing said first and second electrical signals to remove common-mode noise;

said means for splitting said beam of light into two beams of light including a quartz beam splitter positioned at an angle of approximately ten degrees from the incident light;

said means for forming including aperture stops on a flow cell and an aperture plate;

said aperture stops and aperture plate have apertures in them for receiving respectively said first beam of light and said second beam of light;

said aperture stops and apertures being of such a size as to have the image of said aperture and said aperture plate fall within each of them;

means for converting said first and second electrical signals into signals having an amplitude which is the log of the amplitude of said first and second signals; and feedback means for feeding the log of one of said first and second signals back to said light source for regulating the intensity thereof.

13. Apparatus comprising:

a light source;

focusing means for focusing light from a first small spot on said light source onto a second small spot;

an aperture plate having a relatively small aperture in it;

said aperture plate being placed at a location where said aperture in it coincides with said second small spot;

means for splitting the light passing through said aperture into two beams of light;

said means for splitting the light passing through said aperture including a quartz beam splitter positioned with its surface at an angle of approximately 10 degrees to the normal to the direction of the light passing through the aperture;

means for converting said two beams of light into first an second electrical signals;

means for converting one of said first and second electrical signals into a third electrical signal having an amplitude which is the log of the amplitude of said one of said first and second signals; and feedback means for feeding said third signal back to said light source for regulating the intensity thereof.

14. Apparatus comprising a light source;

focusing means for focusing light from a first small spot on said light source onto a second small spot;

an aperture plate having a relatively small aperture in it;

said aperture plate being placed at a location where said aperture in it coincides with said second small spot;

means for splitting the light passing through said aperture into first and second beams of light;

means for converting said first and second beams of light into first and second electrical signals;

means for converting one of said first and second electrical signals into a third electrical signal having an amplitude which is the log of the amplitude of said one of said first and second electrical signals; and feedback means for feeding the log of said third electrical signal back to said light source for regulating the intensity thereof.

15. Apparatus comprising:

a light source;

means for forming a beam of light from the light in said light source;

means for splitting said beam of light into first and second beams of light without substantial alteration of the polarization of the light;

means for using said first and second beams of light to measure a characteristic of a substance;

means for bringing said first of said beams of light into intimate contact with a sample;

means for converting said first of said beams of light into a first electrical signal after it has been brought into intimate contact with a sample;

means for converting the second of said beams of light into a second electrical signal;

means for comparing said first and second electrical signals to remove common-mode noise;

said means for splitting said beam of light into two beams of light including a quartz beam splitter positioned at an angle of approximately ten degrees from the incident light;

said means for splitting a beam of light including aperture stops on a flow cell and an aperture plate;

said aperture stops and aperture plate having apertures in them for receiving respectively said first beam of light and said second beam of light;

said aperture stops and apertures being of such a size as to have the image of said aperture and said aperture plate fall within each of them;

means for converting said first and second electrical signals into signals having an amplitude which is the log of the amplitude of said first and second signals; and feedback means for feeding the log of one of said first and second signals back to said light source for regulating the intensity thereof.

16. Apparatus comprising:

a light source;

means for forming a beam of light from the light in said light source;

means for splitting said beam of light into first and second beams of light without substantial alteration of the polarization of the light;

means for using said first and second beams of light to measure a characteristic of a substance;

said means for splitting said beam of light into two beams of light including a quartz beam splitter positioned at an angle of approximately ten degrees from the incident light and aperture stops on a flow cell and an aperture plate;

said aperture stops and aperture plate having apertures in them for receiving respectively said first beam of light and said second beam of light;

said aperture stops and apertures being of such a size as to have the image of said aperture and said aperture plate fall within each of them;

means for converting said first and second electrical signals into signals having an amplitude which is the log of the amplitude of said first and second signals; and feedback means for feeding the log of one of said first and second signals back to said light source for regulating the intensity thereof.

17. Apparatus comprising:

a light source;

means for forming a beam of light from the light in said light source;

means for splitting said beam of light into first and second beams of light without substantial alteration of the polarization of the light;

means for using said first and second beams of light to measure a characteristic of a substance;

said means for splitting a beam of light including aperture stops on a flow cell and an aperture plate;

said aperture stops and aperture plate having apertures in them for receiving respectively said first beam of light and said second beam of light;

said aperture stops and apertures being of such a size as to have the image of said aperture of said aperture plate fall within each of them;

means for converting said first and second electrical signals into signals having an amplitude which is the log of the amplitude of said first and second signals; and feedback means for feeding the log of one of said first and second signals back to said light source for regulating the intensity thereof.

18. Apparatus comprising:

a light source;

means for forming a beam of light from the light emitted by said light source;

means for splitting said beam of light into first and second beams of light;

means for bringing said first beam of light into intimate contact with a sample;

means for converting said first beam of light into a first electrical signal after it has been brought into intimate contact with a sample;

means for converting said second beam of light into a second electrical signal;

means for converting said first and second electrical signals into signals having an amplitude which is the log of the amplitude of said first and second signals;

means for feeding back the log signal of one of said first and second signals to said source of light to control the intensity of said source of light; and means for comparing the logs of said first and second electrical signals to remove common-mode noise.

19. Apparatus according to claim 18 further comprising means for forming a beam of light from the light passing through said aperture and splitting said beam of light into first and second beams of light, without substantial polarization of the light.

* * * * *